United States Patent
Miller et al.

(10) Patent No.: US 9,328,315 B2
(45) Date of Patent: May 3, 2016

(54) PROCESS FOR SEPARATION OF A PROCESSED VEGETABLE FAT

(75) Inventors: Rasmus Leth Miller, Viby J (DK);
Mogens Bach, Aarhus (DK)

(73) Assignee: AAK AB, Malmo (SE)

(*) Notice: Subject to any disclaimer, the term of this patent is extended or adjusted under 35 U.S.C. 154(b) by 0 days.

(21) Appl. No.: 14/426,706

(22) PCT Filed: Sep. 7, 2012

(86) PCT No.: PCT/DK2012/050336
§ 371 (c)(1),
(2), (4) Date: Mar. 6, 2015

(87) PCT Pub. No.: WO2014/037008
PCT Pub. Date: Mar. 13, 2014

(65) Prior Publication Data
US 2015/0267142 A1    Sep. 24, 2015

(51) Int. Cl.
| | |
|---|---|
| *A23D 9/00* | (2006.01) |
| *C11B 3/12* | (2006.01) |
| *C11B 7/00* | (2006.01) |
| *C11C 1/00* | (2006.01) |
| *C11C 1/10* | (2006.01) |
| *C12P 7/64* | (2006.01) |

(52) U.S. Cl.
CPC ... *C11B 3/12* (2013.01); *C11B 7/00* (2013.01); *C11B 7/0016* (2013.01); *C11C 1/005* (2013.01); *C11C 1/10* (2013.01); *C12P 7/6454* (2013.01)

(58) Field of Classification Search
CPC .......... C11B 3/12; C11B 7/00; C11B 7/0016; C11B 1/005; C11B 1/10; C12P 7/6454
USPC ........................................................ 554/227
See application file for complete search history.

(56) References Cited

U.S. PATENT DOCUMENTS

2005/0090676 A1    4/2005    Heck et al.

FOREIGN PATENT DOCUMENTS

| EP | 2 319 329 A1 | 5/2011 |
| WO | WO 99/57990 | 11/1999 |
| WO | WO 9957990 A1 * | 11/1999 |

OTHER PUBLICATIONS

International Search Report of International Application No. PCT/DK2012/050336, dated Jun. 14, 2013.

*Primary Examiner* — Deborah D Carr
(74) *Attorney, Agent, or Firm* — Finnegan, Henderson, Farabow, Garrett & Dunner LLP (57) ABSTRACT

The invention relates to a process for separation of a processed vegetable fat (PVF), wherein said process comprises the steps of:

in a distillation step (DIS), distilling the processed vegetable fat (PVF) into a distillate part (DPT) comprising stearic and oleic acid and/or esters thereof, and a distilled vegetable fat (DVF);

in a first fractionation step (DFR), fractionating the distilled vegetable fat (DVF) into a first higher melting point fraction (FHF) being rich in tri-stearate triglycerides (StStSt, where St=stearic acid) and di-stearate diglycerides (StSt) and a first lower melting point fraction (FLF); and in a second fractionation step, fractionating the first lower melting point fraction (FLF) into a second higher melting point fraction (SHF) being rich in 1,3-distearyl-2-oleyl-triglycerides (StOSt, where O=oleic acid), and a second lower melting point fraction (SLF) being rich in 1-stearyl-2,3-dioleyl-triglycerides (StOO) and trioleate-triglycerides (OOO) in a solvent fractionation process (SFR).

The invention furthermore relates to a vegetable fat product obtained from such process.

26 Claims, 4 Drawing Sheets

PROCESS FOR SEPARATION OF A PROCESSED VEGETABLE FAT

This application is a national stage filing under 35 U.S.C. §371 of International Application No. PCT/DK2012/050336 filed on Sep. 7, 2012, the contents of which is incorporated herein by reference.

FIELD OF THE INVENTION

The invention relates to a process according to claim 1.

BACKGROUND OF THE INVENTION

It is known to separate vegetable fat by fractionation. However, a number of problems exist in relation to such a fractionation and to a fractionated fat obtained by such fractionation. It is therefore an object of the invention to provide a process for separation, which is efficient and cost-effective.

SUMMARY OF THE INVENTION

The invention relates to a process for separation of a processed vegetable fat, wherein said process comprises the steps of
- in a distillation step distilling the processed vegetable fat into a distillate part comprising stearic and oleic acid and/or esters thereof, and a distilled vegetable fat,
- in a first fractionation step fractionating the distilled vegetable fat into a first higher melting point fraction being rich in tri-stearate triglycerides (StStSt, where St=stearic acid) and di-stearate diglycerides (StSt) and a first lower melting point fraction, and
- in a second fractionation step fractionating the first lower melting point fraction into a second higher melting point fraction being rich in 1,3-di-stearyl-2-oleyl-triglycerides (StOSt, where O=oleic acid), and a second lower melting point fraction being rich in 1-stearyl-2,3-dioleyl-triglycerides (StOO) and trioleate-triglycerides (OOO) in a solvent fractionation process.

One advantage of the invention is that by separating StStSt triglycerides and StSt diglycerides as the solid first higher melting point fraction, the fraction, which is to be fractionated in the second fractionation, namely the first lower melting point fraction, is obtained as a liquid output. Such a liquid fraction may be substantially easier to handle compared to a solid fraction, since it can be pumped, and therefore transported with significantly less effort compared to a solid fraction. Thus, by removing a solid fraction, which typically may make up only a lesser fraction of the distilled vegetable fat, and which is more difficult to handle and transport, and feeding the liquid fraction further onto the next processing step, an advantageous separation process is obtained.

Another advantage of the invention is obtained by allowing the use of, first, a dry fractionation to separate StStSt triglycerides and StSt diglycerides, and, second, a solvent fractionation to obtain an StOSt rich fraction. The first fraction may typically divide the processed vegetable fat into a large first lower melting point fraction, which is liquid, and a smaller first higher melting point fraction, which is solid. By feeding a substantial part of the processed vegetable fat onto the second fractionation as a liquid fraction, namely the first lower melting point fraction, the two fractionation steps may be linked in an efficient way to facilitate transportation between the two fractionation steps. Here. it should be understood that by linked may not necessarily be meant a physical link of the process equipment, but also that the two fractionation steps can be performed efficiently after one another, and therefore, that transportation between the two steps and optionally one or more storage tanks is optimized. In practice, it may often be an advantage to use an intermediate storage tank between the two fractionation steps. Furthermore, the two fractionations may be performed continuously, semi-continuously, or batch-wise. Typically, a dry fractionation may be operated batch-wise, while a solvent fractionation may be operated continuously, however, in some embodiments, this may not apply. This permits setups where the two fractionation steps are separated, but connected by piping and/or intermediate storage tanks, while it renders manual handling of the output from the first fractionation, which is to be fed into the second fractionation, obsolete. Furthermore, by separating a less valuable first higher melting point fraction, which may typically be used in lower value products, as a solid fraction in lesser amounts, such solid fraction provides no or lesser handling problems, as this first higher melting point fraction and the handling of this is not or less critical. Thereby, an efficient and cost-effective separation process is obtained.

By a fractionation is meant a process of heating until the fat to be fractionated is completely melted, then cooling until a part of the fat to be fractionated crystallized, i.e. separation by crystallization. Therefore, one could e.g. describe the fractionation as a fractional crystallization. The cooling may be accompanied by minor heating steps, and the cooling could therefore be described as a temperature regulation step, in which the final temperature is less than the initial temperature. In such a temperature regulation step, the cooling and/or heating rate may be varied, and the temperature regulation step may also comprise steps of keeping the temperature constant. It is to be understood that when using a solvent fractionation process, the solvent will subsequently be removed from the resulting fractions.

It should be noted that the StOSt is to be understood as the symmetric 1,3-distearyl-2-oleyl-triglycerides. Furthermore, StOO is 1-stearyl-2,3-dioleyl-triglycerides, StStSt refers to tri-stearate triglycerides, OOO to tri-oleate triglycerides, and StSt to di-stearate diglycerides comprising 1,2-distearate diglycerides and 1,3-distearate diglycerides. Similarly, StO and OO diglycerides may comprise both the 1,2- and the 1,3- versions.

According to an embodiment of the invention, said process comprises an enzymatic transesterification step of feeding the initial input vegetable fat and a stearic acid source into a reaction system, in which said processed vegetable fat is produced from the initial input vegetable fat and the stearic acid source under influence of enzymes having 1,3-specific transesterification activity, and a step of feeding the processed vegetable fat obtained from the reaction system into the distillation step.

The stearic acid source could e.g. be stearic acid itself, or an ester thereof, such as an alkyl ester, preferably a lower alkyl ester, more preferably e.g. a methyl or ethyl ester, most preferably a methyl ester of stearic acid. Furthermore, there is a connection between the source of stearic acid and the form of oleic acid that can be distilled from the transesterified processed vegetable fat. E.g. when using esters of stearic acid, the oleic acid may be obtained in the same form, i.e. as esters; and if e.g. methyl esters of stearic acid are used, methyl esters of oleic acid may be obtained by the distillation. Furthermore, of course the unreacted part of the stearic acid source may also be obtained by the distillation.

According to an embodiment of the invention, the reaction system produces said processed vegetable fat on the basis of an input vegetable fat, a stearic acids source, and enzymes having 1,3-specific transesterification activity.

The processed vegetable fat may advantageously be provided by means of a transesterification process where stearic acid from a stearic acid source such as an ester of stearic acid, is substituted onto position 1 or 3 on the triglycerides of the input vegetable fat by a catalytic process involving the enzymes, i.e. under the influence of 1,3-specific enzymes.

In the present context, the inventive process is particularly advantageous when used with an input vegetable fat obtained from shea butter and a source of stearic acid due to the fact that the remaining process may fit well into the specific compositions available when working on the basis of e.g. an olein fraction obtained from shea butter.

According to an embodiment of the invention, the distillate part comprising the stearic and oleic acid and/or esters thereof distilled from the processed vegetable fat is fed back in said reaction system and is used at least partly as a stearic acid source for the transesterification in said reaction system.

A very interesting benefit of this feedback of the stearic and oleic acid and/or esters thereof, hereunder the feedback of stearic acid and/or esters thereof, is of course that the stearic acid or esters thereof may be reused, but it is also very important that the removal of fatty acids and/or esters thereof makes the following dry and solvent fractionation steps more effective. Furthermore, it is an advantage that fatty acids and/or esters thereof are effectively removed from the feeding lines as early as possible after the addition of fatty acids and/or esters thereof. Finally, the feedback of fatty acids and/or esters thereof is particularly advantageous when the oleic acid and/or esters thereof are converted into stearic acid and/or esters thereof, i.e. when the double bond in oleic acid is saturated, e.g. by hydrogenation of the oleic acid esters.

It is particularly advantageous when the content of fatty acids and/or esters thereof in the distilled vegetable fat is below 1% by weight. In this context it should of course be understood that fatty acids are understood as free fatty acids and not fatty acids in e.g. triglycerides, and likewise that esters of these fatty acids are to be understood as e.g. alkyl esters, such as e.g. methyl or ethyl esters of free fatty acids, and not as glycerol esters of fatty acids, i.e. triglycerides or diglycerides.

Especially, it is advantageous in relation to the above to remove esters of stearic acid and/or oleic acid, such as e.g. stearic acid methyl esters and/or oleic acid methyl esters.

According to an embodiment of the invention, said distillate part is fed through a hydrogenation step before being fed back in said reaction system.

According to the above embodiment, the distillate part is fed through a hydrogenation step before the stearic acid and/or esters thereof in the distillate part are used as a stearic acid source in the transesterification step. By hydrogenating the distillate part, unsaturated fatty acids in the form of free fatty acids or esters are hydrogenated and thereby converted into saturated fatty acids in the respective form.

Since the transesterification reactions produces oleic acid and/or esters thereof, these will at least partly be converted by hydrogenation into stearic acid in the corresponding form. Thereby, the applicability of the distillate to be used as the stearic acid source is increased in an advantageous way.

According to an embodiment of the invention, wherein the process comprises a subsequent step of
  feeding the second lower melting point fraction back into said reaction system.

By feeding the separated second lower melting point fraction back into the reaction system and using this at least partly as a source of input vegetable fat, it is possible to use a second lower melting point fraction, which otherwise may be superfluous, at least partly in the reaction system, thereby increasing the efficiency and output of the enzymatic transesterification.

It should be noted that this absence of fatty acids and/or esters thereof in the distilled fat and the immediate possible reuse of the fatty acids and/or esters thereof in the reaction system is not only beneficial for the initial transesterification, but also very attractive when performing the two subsequent fractionation steps.

One advantage of the above embodiment is obtained by using, first, a solvent fractionation to separate StOSt triglycerides from StOO and OOO triglycerides, then a solvent fractionation to obtain an StOSt rich fraction. The second fractionation may typically divide the first lower melting point fraction into a second lower melting point fraction, which is liquid, and a second higher melting point fraction, which is solid. By feeding the liquid fraction, namely the second lower melting point fraction, back into the transesterification, the process may secure that the fractions, which are to be processed further, are the liquid fractions, which are relatively easy to handle. Thereby, an efficient and cost-effective separation process is obtained.

According to an embodiment of the invention, the stearic acid source comprises stearic acid esters.

It is preferred that the stearic acid source is stearic acid esters, thus the stearic acid, oleic acid and/or esters thereof obtained by distillation may be partly esters of stearic acid, which are an unreacted part of the stearic acid source, and partly esters of oleic acid, which are products of the transesterification reactions. However, in an alternative embodiment, the stearic acid source may be e.g. stearic acid.

According to an embodiment of the invention, the distilled vegetable fat comprises less than 1% by weight of free fatty acid and/or esters.

In relation to the above embodiment, it should be mentioned that free fatty acids and/or esters thereof particularly relates to stearic and oleic acid and/or esters thereof, i.e. the stearic acid source and the resulting oleic acid or esters thereof produced in the transesterification process.

According to an embodiment of the invention, the distilled vegetable fat comprises between 0 and 1 percent by weight of stearic acid, oleic acid, and/or esters thereof.

According to an embodiment of the invention, the stearic acid, oleic acid, and/or esters thereof are distilled completely off the processed vegetable fat in the distillation.

In the present context it should be understood that the minor amount of fatty acids and/or esters thereof will probably always be present in the distilled fat, but now in a relatively insignificant amount. Such insignificant amount may be less than 0.9%, less than 0.8%, less than 0.6%, less than 0.5% or even less than 0.4% by weight of the distilled fat. This is especially preferred when the stearic acid source is esters of stearic acid.

According to an embodiment of the invention, the concentration of StSt diglycerides in the second higher melting point fraction is less than 5 percent by weight, preferably less than 4 percent by weight, more preferably less than 3 percent by weight, more preferably less than 2 percent by weight, more preferably less than 1.5 percent by weight, such as less than 1 percent by weight, such as less than 0.8 percent by weight, such as less than 0.6 percent by weight, such as less than 0.4 percent by weight, such as less than 0.2 percent by weight.

An advantage of the invention is that the concentration of di-stearate diglycerides is lowered. Moreover, by lowering the concentration of di-stearate diglycerides, the second higher melting point fraction may have improved crystallization properties, and may therefore have an improved applicability as a confectionary fat or a component thereof, thereby increasing the value of the second higher melting point fraction. Also, by lowering the concentration of tri-stearate triglycerides, the second higher melting point fraction may have improved crystallization properties and/or be suitable or more suitable for confectionary fat.

Also, since StSt may give rise to disadvantageous process technical effects, it is an advantage of the above embodiment that the concentration of StSt may be lowered. Such disadvantageous process technical effects comprise that a fat composition may foam more extensively due to the presence of StSt diglycerides. Therefore, by removing StSt diglycerides or at least lowering the concentration of StSt diglycerides, the advantage of removing or at least minimizing the foaming is obtained.

Furthermore, it should be noticed that the above described fractionation process has the benefit of efficiently removing high melting point StStSt triglyceride and StSt diglycerides from the distilled vegetable fat at the same time.

An advantage of the above embodiment is that a disadvantage of enzymatically transesterified vegetable fat products may be overcome. Water content in the oil to be transesterified is typically required in order to achieve sufficient lifetime of enzymes. However, the water content gives rise to formation of diglycerides in the transesterification process. Therefore, it may be difficult to achieve satisfactory lifetime of the enzymes, while at the same time keeping the concentration of diglycerides low. This disadvantage is mitigated by means of the above embodiment.

According to an embodiment of the invention, the concentration of StSt diglycerides in the first lower melting point fraction is less than 3 percent by weight, preferably less than 2 percent by weight, more preferably less than 1.5 percent by weight, such as less than 1 percent by weight, such as less than 0.8 percent by weight, such as less than 0.6 percent by weight, such as less than 0.4 percent by weight, such as less than 0.2 percent by weight.

According to an embodiment of the invention, the second higher melting point fraction is subjected to a step of removing esters of stearic and/or oleic acid.

An advantage of the above embodiment is that by removing the fatty acid alkyl esters, such as esters of stearic acid and/or oleic acid, the product may be acceptable as a food or food ingredient. By partly removing the fatty acid alkyl esters, the product may more easily be modified into a food or food ingredient by subsequent processing, such as e.g. a deodorization process. It is to be understood that the second higher melting point fraction has only a low content of fatty acid esters, such as esters of stearic and oleic acid, since these are mostly removed by the distillation process. However, a small amount of fatty acid esters may remain in the distilled vegetable fat and therefore it is an advantage to remove these from the valuable second higher melting point fraction, e.g. due to food regulations.

According to an embodiment of the invention, the second higher melting point fraction is subjected to a deodorization step.

Such a deodorization step may comprise removal of various undesirable compounds. Such undesirable compounds may be harmful to e.g. the taste, smell, and/or crystallization characteristics of the second higher melting point fraction or a confectionary product thereof, such as e.g. a chocolate. Furthermore, it is advantageous that the deodorization may remove fatty acid alkyl esters, which may be necessary in order to use the second higher melting point fraction as a food ingredient. However, it should be noted that the deodorization process may have a limited capacity for removing fatty acid esters, and therefore the distillation step together with the deodorization removes the fatty acid esters. Therefore, it may be preferred to distill away from the processed vegetable fat most of the fatty acid esters, and then to remove the last part of the fatty acid esters in the deodorization process. Likewise, the deodorization may be able to remove fatty acids, such as stearic or oleic acid.

According to an embodiment the deodorization process may e.g. remove volatile substances, such as free fatty acids and/or esters thereof, pigments, and/or oxidation products. The deodorization process may comprise leading steam through the substance to be deodorized, such as the second higher melting point fraction. This may preferably be done at a high temperature of the steam and/or of the second higher melting point fraction. Furthermore, this is preferably done in a vacuum. A further advantage of the deodorization step may be that second higher melting point fraction may have a brighter color after the deodorization step.

According to an embodiment of the invention, the distilled vegetable fat has a relative content of free fatty acids and/or esters thereof being lower than 1 percent by weight.

An advantage of the above embodiment is that by having a low content of fatty acid alkyl esters, such as esters of steric and/or oleic acid, less fatty acid alkyl esters have to be removed in order to obtain a final product suitable as a food ingredient free of fatty acid alkyl esters. Therefore, it may be an advantage to remove or at least minimize the concentration of fatty acid alkyl esters before the first fractionating. The concentration of fatty acid alkyl esters may in example embodiments be e.g. 0.9 percent by weight, 0.8 percent by weight, 0.7 percent by weight, 0.6 percent by weight, or 0.5 percent by weight. However, in alternative embodiments the relative content of free fatty acids and/or esters thereof in the distilled vegetable fat is lower than 2 percent by weight.

According to an embodiment of the invention, the distilled vegetable fat has a relative content of free fatty acids and/or esters thereof being lower than 0.5 percent by weight.

An advantage of the above embodiment is that by having a low content of fatty acid alkyl esters, less fatty acid alkyl esters have to be removed in order to obtain a valuable second higher melting point fraction free of fatty acid alkyl esters. Therefore, it may be an advantage to remove or at least minimize the concentration of fatty acid alkyl esters before the first fractionating. The concentration of fatty acid alkyl esters may in example embodiments be e.g. 0.4 percent by weight, 0.3 percent by weight, 0.2 percent by weight, or 0.1 percent by weight.

According to an embodiment of the invention, the fractionation process is a dry fractionation process.

One advantage of the above embodiment is obtained by using first a dry fractionation to separate StStSt triglycerides and StSt diglycerides, then a solvent fractionation to obtain an StOSt rich fraction. The first fraction may typically divide the processed vegetable fat into a large first lower melting point fraction, which is liquid, and a smaller first higher melting point fraction, which is solid. By feeding a substantial part of the processed vegetable fat onto the second fractionation as a liquid fraction, namely the first lower melting point fraction, the two fractionations may be linked in an efficient way to facilitate transportation between the two fractionation steps. Here. it should be understood that by linked may not necessarily be meant a physical link of the process equipment, but also that the two fractionation steps can be performed efficiently after one another, and therefore, that transportation between the two steps and optionally one or more storage tanks is optimized. In practice, it may often be an advantage to use an intermediate storage tank between the two fractionation steps. Furthermore, the two fractionations may be performed continuously, semi-continuously, or batch-wise. Typically, a dry fractionation may be operated batch-wise, while a solvent fractionation may be operated continuously, however, in some embodiments, this may not apply. This permits setups where the two fractionations are separated, but connected by piping and/or intermediate storage tanks, while it renders manual handling of the output from the first fractionation, which is to be fed into the second fractionation, obsolete. Furthermore, by separating a less valuable first higher melting point fraction, which is typically used in lower value products, such as animal feed, after the separation, as a solid fraction in lesser amounts, such solid fraction provides no or lesser handling problems, as this first higher melting point fraction and the handling of this is less critical. Thereby, an efficient and cost-effective separation process is obtained.

Another advantage of using a dry fractionation as the first fractionation is that such a dry fractionation may typically be substantially cheaper, both in relation to equipment costs and in relation to operational costs. Thereby, a more costs-effective overall process may be obtained, while using a solvent fractionation as a second fractionation to achieve a relatively well-separated and therefore high-value end product.

According to an embodiment of the invention, the first fractionation step is a solvent fractionation process using a first fractionation solvent.

An advantage of the above embodiment is that when separating processed vegetable fat that poses problems or challenges for dry fractionation, or when particularly high fractionation efficiency is needed, a solvent fractionation process may solve such problems, e.g. due to the high separation efficiency.

According to an embodiment of the invention, the first fractionation solvent comprises hexane.

According to a preferred embodiment, the first fractionation solvent is hexane. However, in alternative embodiments the first fractionation solvent may comprise acetone, methanol, or other suitable solvents.

According to an embodiment of the invention, the dry fractionation comprises the steps of
heating the distilled vegetable fat to a first temperature to melt the distilled vegetable fat, said first temperature being at least the melting temperature of the distilled vegetable fat,
cooling the distilled vegetable fat to a second temperature such that the first higher melting point fraction precipitates from the first lower melting point fraction, and the first lower melting point fraction remains a liquid, and
separating the first higher melting point fraction from the first lower melting point fraction.

According to the above described embodiment, said fractionation is advantageous for separating said first higher melting point fraction and the first lower melting point fraction from each other. By crystallizing higher melting point triglycerides of the distilled vegetable fat, a very clean or chemically well-defined first lower melting point fraction may be obtained, at least with respect to StStSt triglycerides and StSt diglycerides in that these are effectively removed. In the present context it is preferably understood that melting the distilled vegetable fat includes melting the components of the distilled vegetable fat, such as triglycerides.

According to an embodiment of the invention, the step of separating the first higher melting point fraction from the first lower melting point fraction comprises separation by liquid-solid separation.

By separating the first higher melting point fraction from the first lower melting point fraction by liquid-solid separation, an effective separation of the first higher and lower melting point fractions may be obtained. Especially, the first lower melting point fraction may be obtained having a low concentration of higher melting point triglycerides, such as e.g. StStSt, and StSt-diglycerides.

According to an embodiment of the invention, the liquid-solid separation comprises a step of filtering.

By using filtering as a liquid-solid separation, a simple yet efficient solution for liquid-solid separation may be obtained. Alternatively, other means for liquid-solid separation may be used.

According to an embodiment of the invention, said first temperature is at least 15° C. above the second temperature, such as 20° C. degrees above the second temperature.

An advantage of the above embodiment is that no unmelted components or triglycerides are left. Such unmelted components or triglycerides may cause the fat to crystallize into undesirable crystals or crystal forms.

Preferably, said first temperature is at least 20° C. above the second temperature. In example embodiments, the first temperature may be 16° C., 18° C., 20° C., 22° C., 25° C., 30° C., 35° C., or 40° C. above the second temperature.

According to an embodiment of the invention, said first temperature is at least 50° C., such as e.g. 60° C.

An advantage of the above embodiment is that no crystal memory is left. Such crystal memory may cause the fat to crystallize in undesirable crystals. According to one embodiment the first temperature being at least 50° C. is to be understood as between 50° C. and an upper temperature, said upper temperature being e.g. 200° C., 150° C., 100° C., 80° C., 70° C., or 65° C.

Furthermore, the temperature may be between 50° C. and 100° C., such as between 50° and 70° C., such as between 55° C. and 65° C., such as between 58° C. and 62° C., such as 60° C.

In example embodiments, the first temperature may be e.g. 55° C., 57° C., 60° C., 62° C., 65° C., 67° C., or 70° C.

According to an embodiment of the invention, the step of cooling the distilled vegetable fat is performed at a cooling rate, said cooling rate being between 0.1° C. per minute and 3° C. per minute, such as between 0.5 and 1° C./minute.

In an example embodiment, the cooling rate may be between 0.2° C. per minute and 2.5° C. per minute, such as between 0.3° C. per minute and 2.0° C. per minute, preferably between 0.4° C. per minute and 1.5° C. per minute, even more preferably between 0.5° C. per minute and 1.0° C. per minute. Examples of such cooling rates may e.g. be 0.6° C. per minute, 0.7° C. per minute, 0.8° C. per minute, or 0.9° C. per minute.

According to an embodiment of the invention, the step of cooling the distilled vegetable fat comprises at least one cooling cycle, said cooling cycle comprising a step of
cooling by at a cooling cycle cooling rate from a starting temperature to an end temperature.

According to the above embodiment, the cooling cycle starting temperature is the temperature when the cooling cycle starts, and the cooling cycle end temperature is the temperature when the cooling cycle ends. As described, the step of cooling the melted fat comprises at least one additional cooling cycle. The starting temperature of the first of the at least one cooling cycles may be the first temperature, while the end temperature of the final or last cooling cycle is the second temperature. For embodiments with only a single cooling cycle, the starting and end temperature corresponds to the first and second temperatures. The starting temperature of the n'th cooling cycle is preferably the end temperature of the n−1'th cooling cycle, i.e. temperature is preferably not changed between two adjacent cooling cycles.

According to an embodiment of the invention, said cooling cycle furthermore comprises a step of
keeping the temperature constant for a predefined time period after said step of cooling by a first cooling rate.

The predefined time period of the above embodiment may be between 1 minute and 24 hours, preferably between 0.25 and 6 hours, even more preferably between 0.5 and 4 hours, such as 0.5, 0.75, 1, 1.5, 2, 2.5, 3, 3.5, or 4 hours. One advantage of employing a period of constant temperature according to the above embodiment may be that the separation of the fractions, such as liquid-solid separation, may be easier to perform.

According to an embodiment of the invention, said step of cooling the distilled vegetable fat comprises a plurality of cooling cycles.

Preferably, the cooling cycle is performed between 1 and 6 times. As examples of the above embodiment, the step of cooling may comprise e.g. 2, 3, 4, 5, 6, 7, or more of such cycles. Moreover, the cooling rates in the different cycles may be equal to each other, or they may in at least some of the cycles vary from the cooling rates of at least one other cycle. Furthermore, the cooling rates may be constant through a cycle, or they may be varied throughout the individual cycles.

According to an embodiment of the invention, said second temperature is between 20° C. and 40° C.

Further to the above embodiment, the second temperature may preferably be between 23 and 37° C. Examples of the second temperature according to the above embodiment may be e.g. 20° C., 22° C., 24° C., 26° C., 28° C., 30° C., 32° C., 34° C., 36° C., 38° C., 40° C., or any other temperature within the temperature interval of the above embodiment.

According to an embodiment of the invention, the temperature of the distilled vegetable fat is kept constant for a predefined holding time period after cooling the distilled vegetable fat to the second temperature.

According to the above embodiment the predefined holding time period may be between 1 minute and 24 hours, preferably between 0.05 and 10 hours, and even more preferably between 0.1 and 7 hours, such as 0.1, 0.2, 0.5, 0.75, 1, 1.5, 2, 2.5, 3, 3.5, 4, 4.5, 5, 5.5, 6, 6.5, or 7 hours.

According to an embodiment of the invention, the relative content of StStSt and/or StSt in the first higher melting point fraction is increased by lowering at least one cooling rate.

Therefore, according the above embodiment, the first fractionation becomes more effective when lowering at least one cooling rate. However, it should be noticed that lowering the cooling rate also lowers the capacity, and therefore the cooling rate should not be lowered too much. In an embodiment with one cooling rate, this may be lowered to increase the relative content of StStSt and/or StSt in the first higher melting point fraction. In embodiments with several cooling rates in the cooling cycles, lowering at least one of these cooling rates may increase the relative content of StStSt and/or StSt in the first higher melting point fraction.

According to an embodiment of the invention, the relative content of StOSt in the first lower melting point fraction is increased by lowering at least one cooling rate. Therefore, according the above embodiment, the first fractionation becomes more effective when lowering at least one cooling rate. In an embodiment with one cooling rate, this may be lowered to increase the relative content of StOSt in the first lower melting point fraction. In embodiments with several cooling rates, lowering at least one of these cooling rates may increase the relative content of StOSt in the first lower melting point fraction.

According to an embodiment of the invention, the relative content of StOO and/or OOO in the first lower melting point fraction is increased by lowering at least one cooling rate.

In an embodiment with one cooling rate, this may be lowered to increase the relative content of StOO and/or OOO in the first lower melting point fraction. In embodiments with several cooling rates, lowering at least one of these cooling rates may increase the relative content of StOO and/or OOO in the first lower melting point fraction.

According to an embodiment of the invention, the relative content of StSt in the first higher melting point fraction is increased by lowering the second temperature.

According to an embodiment of the invention, the second higher melting point fraction has an improved crystallization characteristics as a component in a cocoa butter equivalent.

According to the above embodiment the second higher melting point fraction may have improved crystallization properties, due to e.g. a lowered concentration of StSt. Such improved crystallization properties may manifest itself in the second higher melting point fraction and/or in a cocoa butter equivalent using the second higher melting point fraction as an StOSt-component. Such improved crystallization properties may increase the value of the second higher melting point fraction, especially when used in a cocoa butter equivalent, where the correct crystallization properties are critical.

According to an embodiment of the invention, said second lower melting point fraction furthermore comprises and mono- or di-unsaturated diglycerides (StO, OO).

According to the above embodiment, mono- and/or di-saturated diglycerides, such as StO or OO diglycerides, may be present in the second lower melting point fraction. Furthermore, these diglycerides may be considerably more present in the second lower melting point fraction compared to the second higher melting point fraction.

According to an embodiment of the invention, said first fractionation comprises the steps of
heating said distilled vegetable fat to a temperature where it is completely melted,
cooling said distilled vegetable fat to a temperature where the first higher melting point fraction crystallizes, and
separating the crystallized first higher melting point fraction from the first lower melting point fraction.

Preferably, the distilled vegetable fat is heated to well above the temperature where it is completely melted, e.g. to a temperature well above the highest melting temperature of the components in the distilled vegetable fat. By well above may be understood e.g. 5° C. above, 10° C. above, 15° C. above, 20° C. above, 25° C. above, 30° C. above or to a higher temperature, or any temperature in between.

According to an embodiment of the invention, said second fractionation comprises the steps of
adding a second fractionation solvent,
heating said first lower melting point fraction to a temperature where it is completely melted,
cooling said first lower melting point fraction to a temperature where the second higher melting point fraction crystallizes, and
separating the crystallized second higher melting point fraction from the second lower melting point fraction.

Preferably, the first lower melting point fraction is heated to well above the temperature where it is completely melted, e.g. to a temperature well above the highest melting temperature of the components in the first lower melting point fraction. By well above may be understood e.g. 5° C. above, 10° C. above, 15° C. above, 20° C. above, 25° C. above, 30° C. above or to a higher temperature, or any temperature in between.

According to an embodiment of the invention, said second fractionation furthermore comprises separating the second fractionation solvent from the second lower melting point fraction.

According to an embodiment of the invention, said second fractionation furthermore comprises separating the second fractionation solvent from the second higher melting point fraction.

According to an embodiment of the invention, the second fractionation solvent comprises acetone.

According to an embodiment of the invention, the second fractionation solvent comprises hexane.

Preferably the second fractionation solvent used in the second fractionation is acetone or hexane. However, other solvents may also be used, such as e.g. methanol, etc. or mixtures of solvents.

According to an embodiment of the invention said input vegetable fat is obtained by refining a crude vegetable fat in a refining step.

By a crude vegetable fat is to be understood a fat which is unprocessed in relation to the present invention, i.e. it may be a fat, which is refined, pre-refined, and/or purified.

According to an embodiment of the invention, the crude vegetable fat comprises shea fat or a fraction thereof, such as a lower melting point fraction of shea fat.

An advantage of the above embodiment is that the content of StSt diglycerides may be lowered in the second higher melting point fraction. This is a particular advantage since shea fat typically has a high content of water, which may be due to e.g. surface active substances. Since a high water content may result in the formation of diglycerides, such as StSt diglycerides, in the transesterification process, it is a particular advantage to fractionate the resulting fat or a part thereof according to the above embodiment of the invention so as to lower the StSt concentration.

According to a further embodiment, the enzymes are lipase, such as a 1,3-specific lipase. Examples of such 1,3-specific lipases may e.g. be lipases of *Rhizopus delemar, Mucor miehei, Aspergillus niger, Rhizopus arrhizus, Rhizopus niveus, Mucor javanicus, Rhizopus javanicus, Rhicomucor miezei* and *Rhizopus oxyzae*. Other 1,3-specific lipases may also be used.

According to an embodiment of the invention, the concentration of StSt in the processed vegetable fat is at least 1.5 percent by weight.

Examples of the concentration of StSt in a processed vegetable fat according the above embodiment may be 1.5 percent by weight, 2 percent by weight, 2.5 percent by weight, 3 percent by weight, 3.5 percent by weight, 4 percent by weight, 4.5 percent by weight, 5 percent by weight, 5.5 percent by weight, 6 percent by weight or even higher. Such fats with StSt content benefit from having the StSt removed so as to increase the value of the processed vegetable fat.

According to an embodiment of the invention, the concentration of StStSt in the first lower melting point fraction is between 0 and 5 percent by weight, such as between 0 and 4 percent by weight, such as between 0 and 3 percent by weight, such as between 0 and 2 percent by weight, such as between 0 and 1 percent by weight, such as between 0 and 0.5 percent by weight, such as between 0 and 0.1 percent by weight.

Thereby, a fraction may be obtained which further to having a low StSt content also may have a low content of StStSt triglycerides.

According to an embodiment of the invention, said second higher melting point fraction is being rich in StOSt, and said second lower melting point fraction is being rich in StOO and OOO.

According to an embodiment of the invention, said second higher melting point fraction has a concentration of StSt diglycerides being between 0 and 4 percent by weight, such as between 0 and 3 percent by weight, such as between 0 and 2 percent by weight, such as between 0 and 1 percent by weight, such as between 0 and 0.5 percent by weight, such as between 0 and 0.2 percent by weight, such as between 0 and 0.1 percent by weight.

As a result of the first fractionation step, the concentration of disaturated diglycerides (StSt) in the first lower melting point fraction may be low. Furthermore, since the concentration of mono- and/or disaturated diglycerides may be lowered by the subsequent second fractionation step, the second higher melting point fraction having an overall low concentration of diglycerides may be obtained. Thereby, the second higher melting point fraction according to example embodiments, may have a concentration of diglycerides being e.g. 0, 0.2, 0.4, 0.6, 0.8, 1, 1.2, 1.4, 1.6, 1.8, 2, 2.2, 2.4, 2.6, 2.8, 3, 3.2, 3.4, 3.6, 3.8, or 4 percent by weight.

According to an embodiment of the invention, said second higher melting point fraction has a concentration of diglycerides being between 0 and 3 percent by weight.

A concentration of no higher than 3 percent may be especially advantageous, particularly for using the second higher melting point fraction in a product with specific crystallization properties, such as a cocoa butter equivalent.

According to an embodiment of the invention, said second higher melting point fraction has a concentration of diglycerides being between 0 and 2 percent by weight.

A concentration of no higher than 2 percent may be especially advantageous, particularly for using the second higher melting point fraction in a product with specific crystallization properties, such as a cocoa butter equivalent.

The invention furthermore relates to a vegetable fat product prepared from a second higher melting point fraction obtained by a process according to any of the above embodiments.

Preferably, the vegetable fat product is the second higher melting point fraction obtained by a process according to an embodiment of the invention.

FIGURES

The invention will be described in the following with reference to the figures in which.

DETAILED DESCRIPTION

Figure 1:
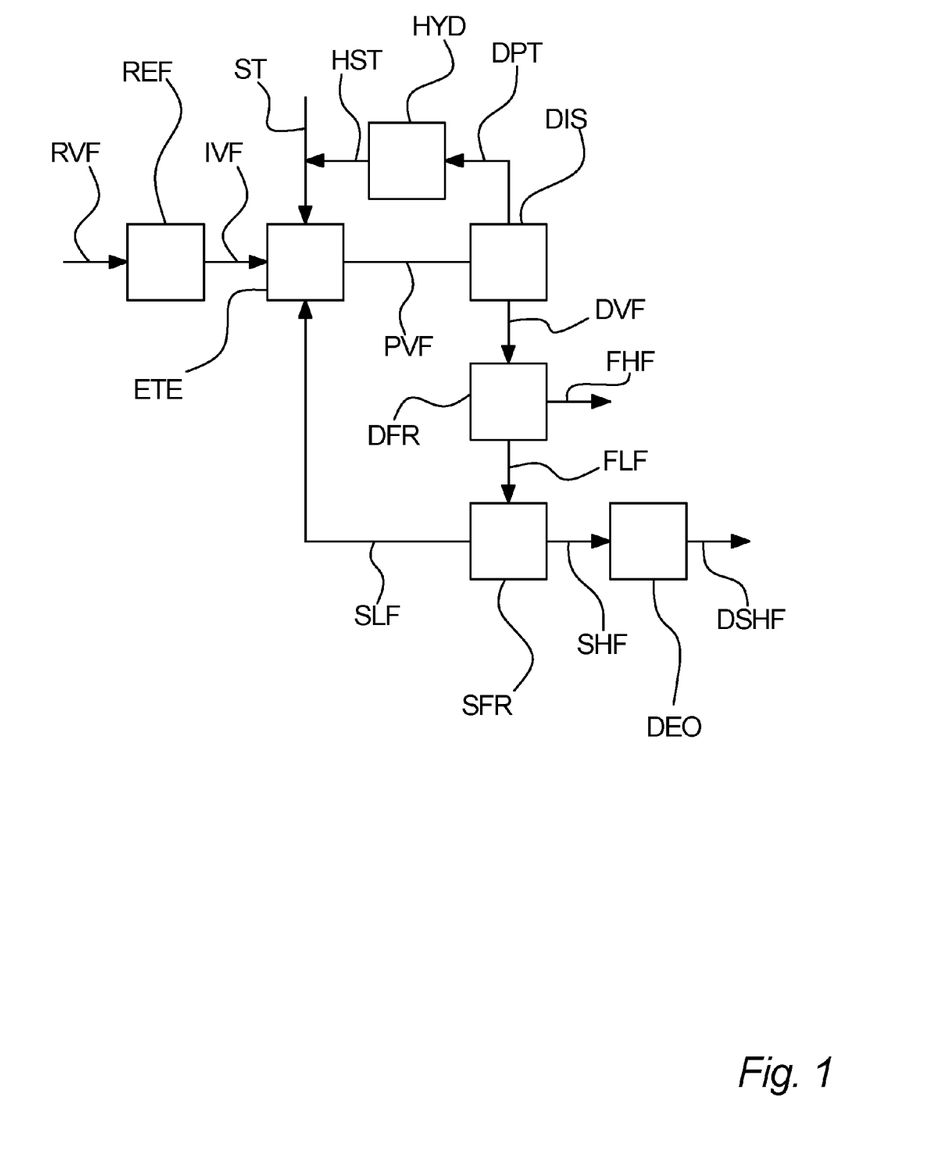
FIG. 1 illustrates a separation process according to an embodiment is illustrated.

Referring to FIG. 1, an embodiment of the invention is illustrated. A crude vegetable fat RVF is fed through a step of refining REF. This refining step REF may e.g. comprise removal of impurities or other unwanted substances. The refining step REF may also comprise separation of the crude vegetable fat RVF into two or more fractions or parts by means of one or more fractionation steps and/or other separation steps. From the refining step REF a refined input vegetable fat IVF is obtained, which is fed into an enzymatic transesterification step ETE. In the enzymatic transesterification step ETE the input vegetable fat IVF is put into contact with enzymes in a reaction system. These enzymes have catalytic activity with respect to a transesterification reaction, and are preferably 1,3-specific enzymes, i.e. their catalytic activity is higher, preferably substantially higher, with respect transesterification on positions 1 and 3 of the triglyceride compared to transesterification on position 2. Also, a stearic acid source ST, such as e.g. stearic acid, methyl stearate (MeSt) or other esters of stearic acid, is fed into the reaction system together with the input vegetable fat IVF. Here it should be noted that in practical setups, the stearic acid source may not be chemically 100% pure; e.g. the stearic acid source ST may comprise up to e.g. 6-10% by weight of fatty acids and/or esters thereof other that stearic acid or esters thereof. For example, e.g. palmitic acid and/or an ester thereof may be present up to e.g. 6-7% by weight. Also, when using a particular form of stearic acid in the stearic acid source ST, stearic acid may also be present in other forms. For example when using methyl ester of stearic acid as stearic acid source ST, the content fatty acid methyl esters may be 90 or 95% by weight, i.e. free fatty acids may be present in amounts up to e.g. 5 to 10% by weight. In various example embodiments, the stearic acid source may comprise stearic acid and/or an ester thereof in amounts of at least 70% by weight, such as at least 80% by weight, such as at least 90% by weight, such as at least 95% by weight, such as at least 98% by weight. However, the stearic acid source is preferably relatively pure, and the purity may e.g. be based on economic considerations of, on one hand, providing a high cost pure stearic acid source and, on the other hand, producing a valuable high purity output. The input vegetable fat IVF comprises triglycerides with an oleic acid on position two and with a fatty acid other than stearic acid on at least one of the positions 1 and 3. This could preferably be StOO and/or OOO, i.e. 1-stearyl-2,3-dioleyl triglycerides and/or trioleate triglycerides. Preferably the input vegetable fat IVF is rich on such fat. In the transesterification process the following reactions are of interest (1)

(2)

In should be noted that reactions (1) and (2) are not to be understood as strict chemical reactions illustrating intermediate steps and/or reaction mechanisms, but rather as an input-output sum of reactions, i.e. the components of the left side may be converted to the components on the right side and vice versa. Furthermore, this application is not limited by theory, such as chemical reactions, which are stated merely to illustrate the invention. As can be seen from reaction (1) and (2), methyl stearate (MeSt) is consumed by the reaction, while methyl oleate (MeO) is formed. Furthermore, the StOO, which may be formed in the first reaction (1) may be converted into StOSt by the second reaction (2). From the enzymatic transesterification a processed vegetable fat PVF is obtained, which is enriched with respect to the content of StOSt, i.e. 1,3-distearyl-2-oleyl triglycerides. This processed vegetable fat PVF is subjected to a distillation step DIS, in which two parts are obtained, namely a distillate part DPT comprising stearic acid esters, which are unreacted stearic acid ester ST, and oleic acid esters, which are formed in the enzymatic transesterification ETE, and a part of a distilled vegetable fat DVF. The distillate part DPT is then subjected to a hydrogenation process HYD, which converts MeO into MeSt by reacting MeO with hydrogen ($H_2$) in the presence of a catalyst, such as e.g. a nickel catalyst. Thereby, hydrogenated stearic acid esters HST are obtained, which is to be understood as stearic acid esters obtained by the distillation DIS and stearic acid esters formed from oleic acid esters in the hydrogenation step HYD. These hydrogenated stearic acid esters may then be fed back into the enzymatic transesterification ETE. The distilled vegetable fat DVF preferably comprises only a very small amount of fatty acid esters, such as below 2 percent by weight, or below 1 percent by weight, or only in trace amounts. The distilled vegetable fat DVF is then subjected to a dry fractionation DFR in which the distilled vegetable fat DVF is fractionated into a first higher melting point fraction FHF and a first lower melting point fraction FLF. In the dry fractionation DFR the distilled vegetable fat DVF is heated such that it is completely melted, e.g. by heating it to 20° C. above the melting temperature of the triglycerides with the highest melting point. Then the melted distilled vegetable fat DVF is cooled according to a temperature profile, causing the triglycerides with the highest melting point to crystallize. These crystallized triglycerides are then separated from the liquid triglycerides, i.e. the triglycerides with lower melting points. It may be very important to heat the triglycerides to a high temperature before cooling in order to secure that the fat is completely melted. Furthermore, the cooling process has to be carried out carefully, since cooling too fast may cause some of the triglycerides to crystallize into undesirable crystalline forms or cause different components in the fat, such as e.g. StOSt and StOO, to co-crystallize, i.e. to form crystalline structures made up of both StOSt and StOO in a certain stoichiometric ratio, which may be rather disadvantageous. By a higher melting point fraction may preferably be meant a fraction, which comprise the triglycerides having a higher melting point, e.g. compared to the unfractionated triglycerides or the triglycerides in the lower melting point fraction. Likewise, a lower melting point may preferably be understood as a fraction comprising triglycerides having a relatively low melting point, e.g. compared to the unfractionated triglycerides or the triglycerides in the higher melting point fraction. Also, or alternatively, a higher melting point fraction may be understood as having a higher melting point compared to the lower melting point fraction and vice versa. Such higher and lower melting point fractions may also be referred to as a stearin and an olein fraction, respectively. The first higher melting point fraction FHF includes mainly tristearate triglycerides (StStSt), and distearate diglycerides (StSt), whereas the first lower melting point fraction FLF includes mainly StOSt, StOO, and OOO triglycerides. The first lower melting point fraction FLF is then subjected to a solvent fraction SFR, where the solvent preferably is hexane or acetone. From the solvent fractionation SFR a second higher melting point fraction SHF and a second lower melting point fraction SLF are obtained. The second lower melting point fraction SLF is fed back into the enzymatic transesterification ETE. Thereby, unreacted StOO and OOO may be transesterified in a second or subsequent passing through the enzymatic transesterification ETE. Also, StOO which was formed by OOO in the enzymatic transesterification ETE may be transesterified into StOSt in another passage through the enzymatic transesterification ETE. The second higher melting point fraction SHF is then subjected to a deodorization DEO. This deodorization DEO may serve several purposes, such as removing impurities and/or unwanted substances, hereunder traces of fatty acid esters, such as methyl stearate (MeSt) and/or methyl oleate (MeO) and/or fatty acids, such as stearic and oleic acid. From the deodorization DEO a deodorized second higher melting point fraction DSHF is obtained. This deodorized second higher melting point fraction DSHF may be suitable for use in a cocoa butter equivalent, due to a high content of StOSt, and furthermore due to a particularly low content StSt diglycerides. Such low StSt-content second higher melting point fraction SHF or DSHF is very suitable for producing a cocoa butter equivalent e.g. together with a palm oil mid fraction (PMF), since such a low StSt-content cocoa butter equivalent has properties equivalent to natural cocoa butter, such as melting properties and crystallization properties etc. On the other hand, a fat fraction with a high content of StStSt triglycerides and/or StSt diglycerides may be unsuitable in a cocoa butter equivalent, due to degraded melting properties and crystallization properties, which may give problems e.g. in the tempering of a chocolate comprising such a cocoa butter equivalent.

Note that a palm oil mid fraction (PMF) may be understood as different palm oil products. Preferably, the PMF should be understood as a hard PMF having an iodine value of 30 to 35, such as 32, 33, or 34. However, in some embodiments, a softer PMF having a higher iodine value of up to e.g. 50 may be usable.

Preferably, the enzymes used in the above reaction system ETE are 1,3-specific enzymes, i.e. enzymes with an increased catalytic activity with respect to a transesterification reaction between a stearic acid from the stearic acid source ST and a fatty acid, such as e.g. oleic acid, on position 1 and 3 on the triglyceride. Therefore, by contacting the stearic acid source ST with the input vegetable fat IVF, such as a lower melting point fraction of shea fat, comprising triglycerides with oleic acid on position 2 with 1,3-specific enzymes, the processed vegetable fat PVF with an increased content of StOSt is produced. This processed vegetable fat PVF may, however, also comprise some diglycerides, such as StSt diglycerides. By fractionating the processed vegetable fat PVF into the first higher melting point fraction FHF and the first lower melting point fraction FLF, a part of the diglycerides can be separated from the fraction rich in StOSt, i.e. from the first lower melting point fraction FLF. This is particularly advantageous when using the second higher melting point fraction SHF derived from this first lower melting point fraction FLF e.g. as an ingredient in cocoa butter equivalent, and furthermore when such cocoa butter equivalent is used in a chocolate or chocolate-like confectionary product. Since the second higher melting point fraction SHF, which is rich in StOSt, may be considerably more valuable compared to a fat fraction which mainly consists of StOO and/or OOO, such as the crude vegetable fat RVF or the input vegetable fat IVF, at least partly due to the crystallization characteristics of StOSt compared to StOO and/or OOO, it is imperative that the crystallization characteristics of the StOSt-rich second higher melting point fraction SHF are retained. However, the presense of StSt diglycerides in even rather small amounts may change the crystallization characteristics of the StOSt-rich second higher melting point fraction SHF so much that the market value of this fraction SHF is substantially diminished. Therefore, by removing the StSt diglycerides by a fractionation DFR, preferably being a dry fractionation DFR, a valuable StO St-rich fat with advantageous characteristics may be produced by e.g. enzymatic transesterification as the second higher melting point fraction SHF. Furthermore, by removing the first higher melting point fraction FHF in the dry fractionation DFR, trisaturated triglycerides StStSt are also removed from the first lower melting point fraction FLF, and therefore also from the second higher melting point fraction SHF. This provides an advantageous process for obtaining an StOSt rich fraction, which has a low content of StStSt triglycerides and StSt diglycerides.

Figure 2:
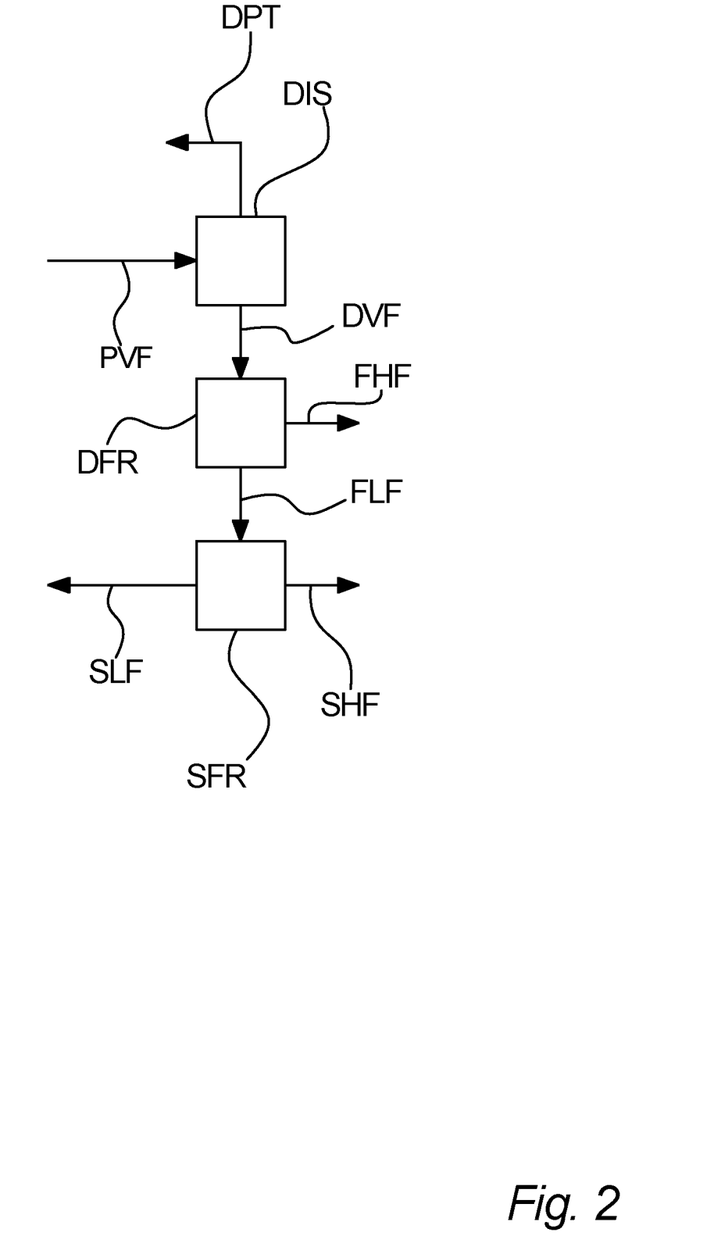
FIG. 2 illustrates a separation process according to an embodiment is illustrated.

Referring to FIG. 2, an embodiment of the invention is illustrated. The embodiment relates to a process for separation of a processed vegetable fat PVF, wherein said process comprises a distillation step DIS of distilling the processed vegetable fat PVF into a distillate DPT comprising stearic and oleic acid and/or esters thereof, and a distilled vegetable fat DVF. Then, in a first fractionation step DFR the distilled vegetable fat DVF is fractionated into a first higher melting point fraction FHF being rich in tri-stearate triglycerides (StStSt, where St=stearic acid) and di-stearate diglycerides (StSt) and a first lower melting point fraction FLF. This first fractionation step is preferably a dry fractionation process DFR, but may also be a solvent fractionation using e.g acetone or hexane as solvent. Then, in a second fractionation step SFR the first lower melting point fraction FLF is fractionated into a second higher melting point fraction SHF being rich in 1,3-distearyl-2-oleyl-triglycerides (StOSt, where St=stearic acid and O=oleic acid), and a second lower melting point fraction SLF being rich in 1-stearyl-2,3-dioleyl-triglycerides (StOO) and trioleate-triglycerides (OOO), using a solvent fractionation process SFR.

Figure 3:
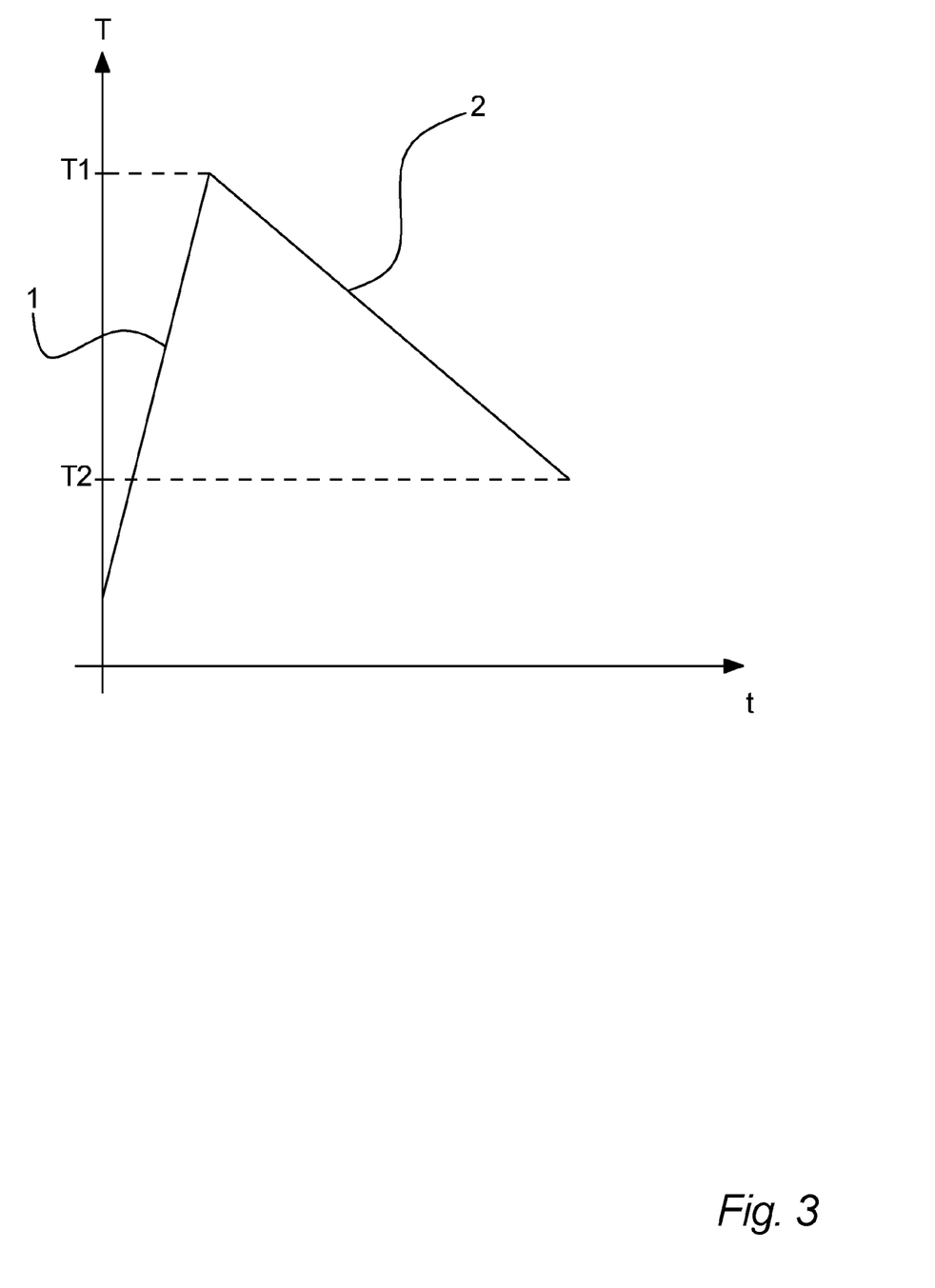
FIG. 3 illustrates a temperature profile according to an embodiment is illustrated.

Referring to FIG. 3, an embodiment of the invention is described. On FIG. 3, a temperature profile is shown. The first fractionation may be performed according to such a temperature profile. The temperature profile may be understood in connection with a temperature regulation step, where a fat to be fractionated is first heated until melted, and then cooled in a temperature regulation step. Such a temperature regulation step may comprise steps of cooling, e.g. with different cooling rates or continuously changing cooling rates, steps of keeping the temperature constant, and even steps of heating. The temperature profile on FIG. 3 shows the evolution of the temperature T of a distilled vegetable fat DVF as a function of time t. As shown on FIG. 3, the distilled vegetable fat DVF is in a first step 1 heated to first temperature T1, at which all the distilled vegetable fat DVF is melted. Preferably, this temperature is sufficiently above the melting temperature of the fat, such as at least e.g. 20° C. above the melting temperature of the fat. Thereby, it is secured that all components of the fat are completely melted, at that no or relatively few solid crystal structures in the fat are left. The distilled vegetable fat DVF is then said to be without any crystal memory. Then, the distilled vegetable fat DVF is in a second step 2 cooled to a second temperature T2. By cooling the distilled vegetable fat DVF to the second temperature T2, high melting point parts of the distilled vegetable fat DVF will crystallize. The crystallized high melting point parts of the distilled vegetable fat DVF may then be separated from the liquid low melting point parts of the distilled vegetable fat DVF by liquid/solid separation, such as e.g. filtering.

Figure 4:
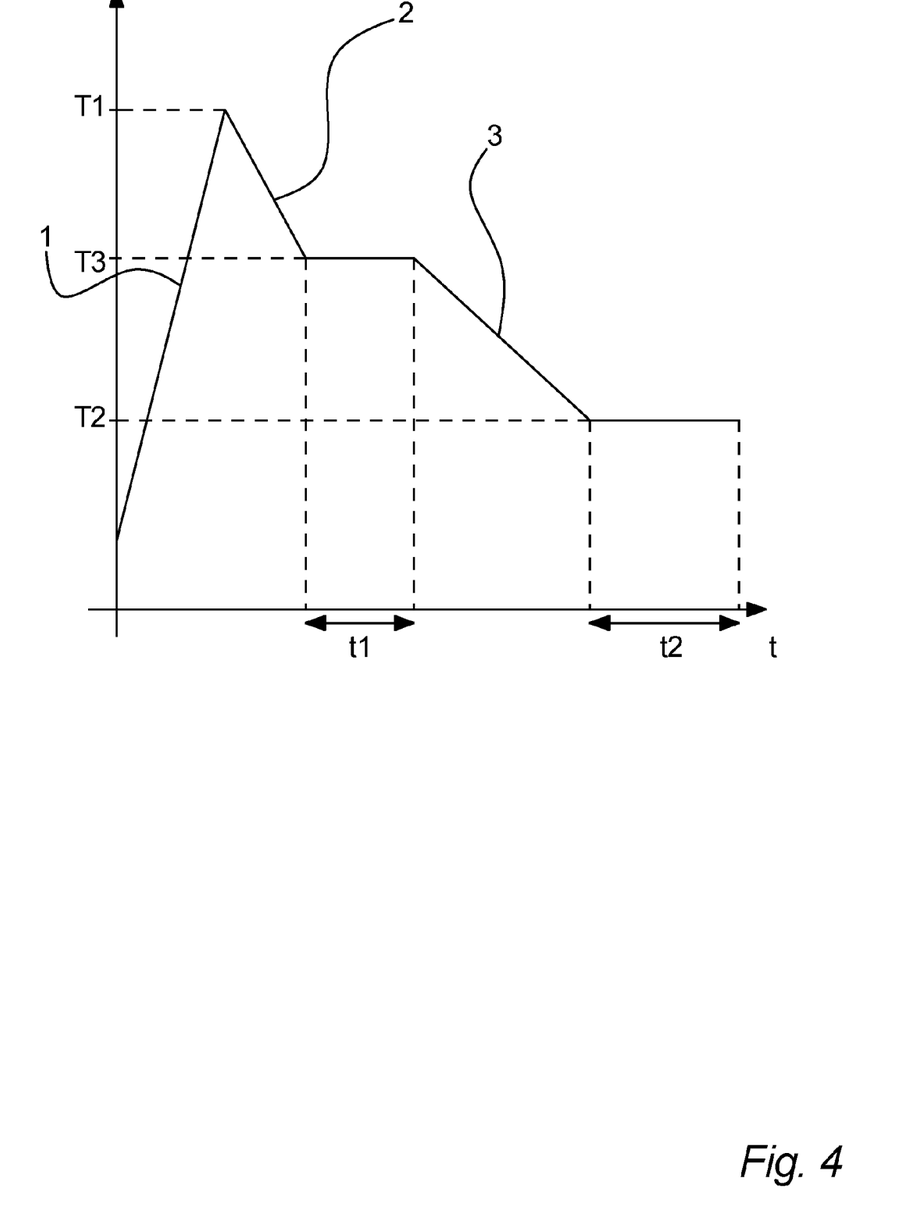
FIG. 4 illustrates a temperature profile according to an embodiment is illustrated.

Now referring to FIG. 4, an embodiment of the invention is illustrated with a more detailed temperature profile. First, the distilled vegetable fat DVF is heated in a first step 1 to a first temperature T1, where the vegetable fat is completely melted. Then, the distilled vegetable fat DVF is cooled in a second step 2 to an intermediate temperature T3, after which the temperature T of the distilled vegetable fat DVF is kept constant for a first period of time t1. Then the temperature T of the distilled vegetable fat DVF is lowered in a third step 3. Finally, the temperature T of the distilled vegetable fat DVF is kept constant in a second period of time t2.

In relation to the above discussion it should be noted that absolute separation of different triglycerides and/or diglycerides is extremely hard to accomplish, especially in industrial scale production. Therefore, when e.g. StSt diglycerides are said to be removed by fractionation, it may in some embodiments be meant that the StSt concentration is lowered sufficiently to remove or at least substantially diminish the disadvantageous characteristics of StSt diglycerides by fractionation.

Example 1

A first sample of an enzymatic transesterified shea olein fraction is subjected to distillation in order to separate unused methyl stearate from the transesterification and methyl oleate, which is a bi-product from the transesterification into a distillate. The distilled first sample is then inputted to a first fractionation, which is a dry fractionation process, the first fractionation giving a first higher melting point fraction and a first lower melting point fraction. The first lower melting point fraction is then subjected to a second fractionation, being hexane solvent fractionation, giving a second higher melting point fraction and a second lower melting point fraction. The concentration of StSt diglycerides in the first sample in for each fraction is measured. These measured concentrations are listed in table I.

TABLE I

|  | Concentration of StSt | Reduction of StSt (abs.) | Reduction of StSt (percentage) |
|---|---|---|---|
| Distilled first sample | 2.8 | N/A | N/A |
| 1st higher melting point fraction | 16.5 | N/A | N/A |
| 1st lower melting point fraction | 0.6 | 2.2 | 79.1 |
| 2nd higher melting point fraction | 1.1 | 1.7 | 61.4 |
| 2nd lower melting point fraction | 0.5 | N/A | N/A |

As can be seen from the concentrations of StSt diglycerides in table I and the absolute and percentage-wise reduction of StSt, the distillation together with the first and second fractionations result in a significant reduction in the concentration of StSt diglycerides in the second higher melting point fraction.

LIST OF FIGURE REFERENCES

RVF. Crude vegetable fat
REF. Refining step
IVF. Input vegetable fat
ST. Stearic acid source
HST. Hydrogenated stearic acid esters
ETE. Enzymatic transesterification
PVF. Processed vegetable fat
DIS. Distillation step
DPT. Distillate part
HYD. Hydrogenation
DVF. Distillated vegetable fat
DFR. Dry fractionation
FHF. First higher melting point fraction
FLF. First lower melting point fraction
SFR. Solvent fractionation
SLF. Second lower melting point fraction
SHF. Second higher melting point fraction
DEO. Deodorization
DSHF. Deodorized second higher melting point fraction
1. First temperature regulation step
2. Second temperature regulation step
3. Third temperature regulation step
4. Fourth temperature regulation step
t. Time
T. Temperature
T1. First temperature
T2. Second temperature
T3. Intermediate temperature
t1. First time period
t2. Second time period

The invention claimed is:

1. A process for separation of a processed vegetable fat (PVF), wherein the process comprises the steps of:
   a distillation step (DIS), distilling the processed vegetable fat (PVF) into a distillate part (DPT), comprising stearic acid or oleic acid or esters thereof, and a distilled vegetable fat (DVF):
   a first fractionation step, fractionating the distilled vegetable fat (DVF) into a first higher melting point fraction (FHF) being rich in tri-stearate triglycerides (StStSt, where St=stearic acid) and di-stearate diglycerides (StSt) and a first lower melting point fraction (FLF); and
   a second fractionation step, fractionating the first lower melting point fraction (FLF) into a second higher melting point fraction (SHF) being rich in 1,3-distearyl-2-oleyl-triglycerides (StOSt, where O=oleic acid), and a second lower melting point fraction (SLF) being rich in 1-stearyl-2,3-dioleyl-triglycerides (StOO) and trioleate-triglycerides (OOO), using a solvent fractionation process (SFR).

2. The process according to claim 1, wherein the process comprises:
   an enzymatic transesterification step of feeding the initial input vegetable fat (IVF) and a stearic acid source (ST) into a reaction system (ETE), which the processed vegetable fat (PVF) is produced from the initial input vegetable fat (IVF) and the stearic acid source (ST) under influence of enzymes having 1,3-specific transesterification activity; and
   a step of feeding the processed vegetable fat (PVF) obtained from the reaction system (ETE) into the distillation step (DIS).

3. The process according to claim 2, wherein the reaction system (ETE) produces the processed vegetable fat (PVF) on the basis of an input vegetable fat (IVF), a stearic acids source (ST), and enzymes having 1,3-specific transesterification activity.

4. The process according to claim 2, wherein the distillate part (DPT) comprising the stearic and oleic acid or esters thereof distilled from the processed vegetable fat (PVF), is fed back in the reaction system (ETE) and is used at least partly as a stearic acid source (ST) for the transesterification activity in the reaction system (ETE).

5. The process according to claim 4, wherein the distillate part (DPT) is fed through a hydrogenation step (HYD) before being fed back in the reaction system (ETE).

6. The process according to claim 1, wherein the process comprises a subsequent step of:
   feeding the second lower melting point fraction (SLF) back into the reaction system (ETE).

7. The process according to claim 2, wherein the stearic acid source (ST) comprises stearic acid esters.

8. The process according to claim 1, wherein the distilled vegetable fat (DVF) comprises less than 1% by weight of free fatty acid, fatty acid esters, or a combination thereof.

9. The process according to claim 1, wherein the second higher melting point fraction (SHF) is subjected to a step of removing esters of stearic acid, oleic acid, or a combination thereof.

10. The process according to claim 1, wherein the second higher melting point fraction (SHF) is subjected to a deodorization step (DEO).

11. The process according to claim 1, wherein the distilled vegetable fat (DVF) has a relative content of free fatty acids, fatty acid esters, or a combination thereof being lower than 1 percent by weight.

12. The process according to claim 1, wherein the first fractionation step is a dry fractionation process (DFR).

13. The process according to claim 1, wherein the first fractionation step is a solvent fractionation process using a first fractionation solvent.

14. The process according to claim 12, wherein the dry fractionation (DFR) comprises the steps of:
   heating the distilled vegetable fat (DVF) to a first temperature (T1) to melt the distilled vegetable fat (DVF), wherein the first temperature (T1) is at least the melting temperature of the distilled vegetable fat (DVF);
   cooling the distilled vegetable fat (DVF) to a second temperature (T2) such that the first higher melting point fraction (FHF) precipitates from the first lower melting point fraction (FLF) and the first lower melting point fraction (FHF) remains a liquid; and
   separating the first higher melting point fraction (FHF) from the first lower melting point fraction (FLF).

15. The process according to claim 14,
   wherein the step of separating the first higher melting point fraction (FHF) from the first lower melting point fraction (FLF) comprises a separation by liquid-solid separation.

16. The process according to claim 14, wherein the step of cooling the distilled vegetable fat (DVF) is performed at a cooling rate, wherein the cooling rate is between 0.1° C. per minute and 3° C. per minute.

17. The process according to claim 14, wherein the second temperature (T2) is between 20° C. and 40° C.

18. The process according to claim 14, wherein the temperature of the distilled vegetable fat (DVF) is kept constant for a predefined holding time period after cooling the distilled vegetable fat (DVF) to the second temperature (T2).

19. The process according to claim 16, wherein the relative content of StStSt, StSt, or a combination thereof in the first higher melting point fraction (FHF) is increased by lowering at least one cooling rate.

20. The process according to claim 16, wherein the relative content of StOSt in the first lower melting point fraction (FLF) is increased by lowering at least one cooling rate.

21. The process according to claim 16, wherein the relative content of StOO or OOO in the first lower melting point fraction (FLF) is increased by lowering at least one cooling rate.

22. The process according to claim 14, wherein the relative content of StSt in the first higher melting point fraction (FLF) is increased by lowering the second temperature (T2).

23. The process according to claim 1, wherein the second fractionation (SFR) comprises the steps of:
   adding a second fractionation solvent;
   heating the first lower melting point fraction (FLF) to a temperature where it is completely melted;
   cooling the first lower melting point fraction (FLF) to a temperature where the second higher melting point fraction (SHF) crystallizes; and
   separating the crystallized second higher melting point fraction (SHF) from the second lower melting point fraction (SLF).

24. The process according to claim 1, wherein the second fractionation (SFR) furthermore comprises the step of separating the second fractionation solvent from the second lower melting point fraction (SLF).

25. The process according to claim 1, wherein the second fractionation (SFR) furthermore comprises the step of separating the second fractionation solvent from the second higher melting point fraction (SHF).

26. The process according to claim 1, wherein the vegetable fat (IVF) is obtained by refining a crude vegetable fat (RVF) in a refining step, wherein the crude vegetable fat (RVF) comprises shea fat or a fraction thereof.

* * * * *